US011957856B2

(12) United States Patent
Melsky et al.

(10) Patent No.: US 11,957,856 B2
(45) Date of Patent: *Apr. 16, 2024

(54) BALLOON CATHETER AND FLUID MANAGEMENT SYSTEM THEREOF

(71) Applicant: CardioFocus, Inc., Marlborough, MA (US)

(72) Inventors: Gerald Melsky, Lexington, MA (US); Brian Estabrook, Foxboro, MA (US); Lincoln Baxter, Centerville, MA (US)

(73) Assignee: CARDIOFOCUS, INC., Marlborough, MA (US)

( * ) Notice: Subject to any disclaimer, the term of this patent is extended or adjusted under 35 U.S.C. 154(b) by 5 days.

This patent is subject to a terminal disclaimer.

(21) Appl. No.: 17/532,434

(22) Filed: Nov. 22, 2021

(65) Prior Publication Data
US 2022/0152365 A1 May 19, 2022

Related U.S. Application Data

(62) Division of application No. 15/863,264, filed on Jan. 5, 2018, now Pat. No. 11,207,505.
(Continued)

(51) Int. Cl.
A61M 25/10 (2013.01)
A61B 18/14 (2006.01)
(Continued)

(52) U.S. Cl.
CPC ... *A61M 25/10184* (2013.11); *A61B 18/1492* (2013.01); *A61M 25/10181* (2013.11);
(Continued)

(58) Field of Classification Search
CPC ...... A61M 25/10184; A61M 25/10181; A61M 25/10185; A61B 18/1492;
(Continued)

(56) References Cited

U.S. PATENT DOCUMENTS 3,570,672 A     3/1971   Bach
3,794,026 A * 2/1974   Jacobs ................. A61M 25/04
                                                                              128/207.15
(Continued)

FOREIGN PATENT DOCUMENTS

AU         2011203584 A1 * 8/2011 ............ A61F 5/442
CN           203107397 U  * 8/2013
WO    WO-2017004432 A1 * 1/2017 ............ A61B 18/02

*Primary Examiner* — Carl H Layno
*Assistant Examiner* — Michael J Lau
(74) *Attorney, Agent, or Firm* — Leason Ellis LLP

(57) ABSTRACT

A balloon catheter device with a fluid management system includes a source of balloon fill media and a balloon catheter in fluid communication with the source of balloon fill media. A first conduit is provided for delivering the balloon fill media from the source to the balloon catheter for inflation of a balloon of the catheter device. A second conduit is provided for returning the balloon fill media from the balloon catheter to the source for deflating the balloon. A first pump is disposed along one of the first conduit and the second conduit for pumping the balloon fill media through the respective conduits. The fluid management system operates in three states, namely, (1) a first state in which the balloon fill media is delivered to the balloon for inflation thereof, (2) a second state in which the balloon fill media is removed from the balloon for deflation thereof; and (3) a trapped volume mode in which the balloon fill media is circulated through the balloon so as to maintain an at least substantially constant pressure in the balloon. The fluid management system is configured to maintain a pressure of the balloon between 0.2 psi and 1 psi while maintaining adequate fluid flow to cool the balloon.

8 Claims, 10 Drawing Sheets

Related U.S. Application Data

(60) Provisional application No. 62/443,270, filed on Jan. 6, 2017.

(51) Int. Cl.
  *A61B 18/00* (2006.01)
  *A61B 18/24* (2006.01)

(52) U.S. Cl.
  CPC .............. *A61B 2018/00023* (2013.01); *A61B 2018/0022* (2013.01); *A61B 2018/00577* (2013.01); *A61B 18/24* (2013.01); *A61M 25/10185* (2013.11)

(58) Field of Classification Search
  CPC .. A61B 2018/00023; A61B 2018/0022; A61B 2018/00577
  USPC ............................................................ 606/27
  See application file for complete search history.

(56) References Cited

U.S. PATENT DOCUMENTS

| | | | |
|---|---|---|---|
| 4,093,545 A | 6/1978 | Cullis | |
| 5,496,311 A | 3/1996 | Abele | |
| 5,746,717 A | 5/1998 | Aigner | |
| 5,759,148 A | 6/1998 | Sipin | |
| 5,833,619 A * | 11/1998 | Freed | A61M 60/468 600/500 |
| 5,861,005 A | 1/1999 | Kontos | |
| 6,082,105 A | 7/2000 | Miyata | |
| 6,135,991 A | 10/2000 | Muni | |
| 6,241,706 B1 * | 6/2001 | Leschinsky | A61M 60/497 604/99.01 |
| 9,033,961 B2 * | 5/2015 | Melsky | A61B 18/245 606/2 |
| 11,207,505 B2 * | 12/2021 | Melsky | A61M 25/10181 |
| 2002/0042701 A1 * | 4/2002 | Dancu | G09B 23/28 703/11 |
| 2002/0116054 A1 * | 8/2002 | Lundell | A61F 2/2472 623/913 |
| 2004/0111138 A1 * | 6/2004 | Bleam | A61F 7/12 607/113 |
| 2005/0209662 A1 * | 9/2005 | Lunderqvist | A61F 7/123 607/113 |
| 2006/0200191 A1 | 9/2006 | Zadno-Azizi | |
| 2006/0265041 A1 | 11/2006 | Sanati | |
| 2006/0271087 A1 * | 11/2006 | Von Dyck | A61M 25/10185 606/192 |
| 2006/0293734 A1 | 12/2006 | Scott | |
| 2007/0032783 A1 * | 2/2007 | Abboud | A61B 18/02 606/22 |
| 2007/0149922 A1 * | 6/2007 | Schneider | A61M 25/10186 604/99.01 |
| 2008/0140001 A1 * | 6/2008 | Globerman | A61M 25/1011 604/97.01 |
| 2008/0177245 A1 * | 7/2008 | Mesallum | A61M 1/3613 604/500 |
| 2009/0012460 A1 | 1/2009 | Stack | |
| 2009/0088735 A1 * | 4/2009 | Abboud | A61M 25/10187 606/22 |
| 2009/0112151 A1 | 4/2009 | Chapman | |
| 2009/0299356 A1 | 12/2009 | Watson | |
| 2010/0049184 A1 | 2/2010 | George | |
| 2010/0049192 A1 * | 2/2010 | Holtz | A61N 1/36071 606/41 |
| 2010/0204765 A1 * | 8/2010 | Hall | A61M 1/288 604/27 |
| 2010/0280451 A1 | 11/2010 | Teeslink | |
| 2011/0190751 A1 | 8/2011 | Ingle | |
| 2011/0202084 A1 * | 8/2011 | Hoem | A61B 17/12122 73/714 |
| 2011/0270175 A1 * | 11/2011 | Ehrenreich | A61M 25/10187 604/99.01 |
| 2012/0071712 A1 * | 3/2012 | Manwaring | A61B 18/10 600/104 |
| 2012/0152842 A1 | 6/2012 | Rada | |
| 2012/0265296 A1 * | 10/2012 | McNamara | A61B 17/11 604/503 |
| 2013/0345688 A1 | 12/2013 | Babkin | |
| 2014/0012368 A1 | 1/2014 | Sugimoto | |
| 2014/0276713 A1 * | 9/2014 | Hoey | A61B 18/04 607/96 |
| 2015/0282858 A1 * | 10/2015 | Baust | A61B 18/02 606/34 |
| 2015/0367036 A1 * | 12/2015 | Schwitzer | A61L 29/06 264/494 |
| 2016/0015947 A1 | 1/2016 | Avevor | |
| 2016/0029998 A1 * | 2/2016 | Brister | A61B 8/0833 600/424 |
| 2016/0114281 A1 | 4/2016 | Bonano | |
| 2016/0279388 A1 * | 9/2016 | Barrish | A61M 25/1036 |
| 2016/0331870 A1 * | 11/2016 | Xie | A61M 25/10 |
| 2016/0354140 A1 * | 12/2016 | Sharma | A61B 90/39 |
| 2017/0021076 A1 | 1/2017 | Lura | |
| 2018/0110342 A1 | 4/2018 | Moss | |
| 2018/0296807 A1 | 10/2018 | Babko-Malyi | |
| 2018/0318543 A1 | 11/2018 | Coleman | |
| 2020/0171226 A1 | 6/2020 | Wilt | |

\* cited by examiner

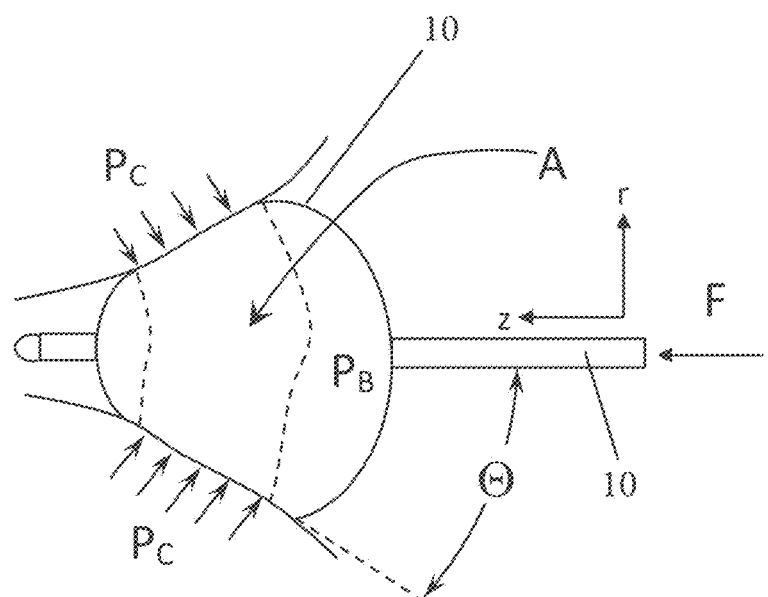
Figure 1 Balloon Forces
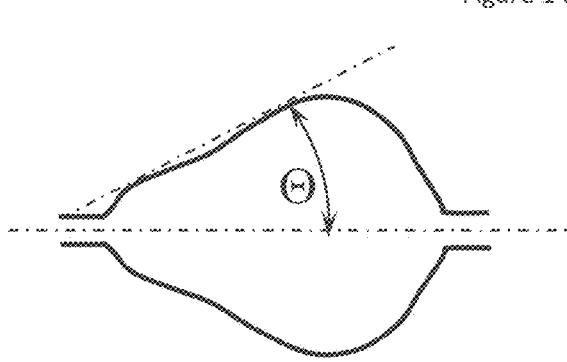
Figure 2 Prior Art Balloon Shape
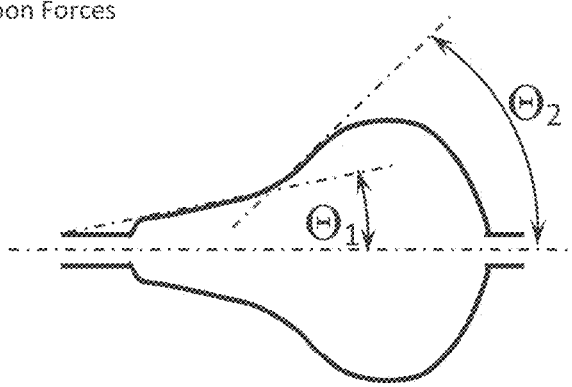
Figure 3 Compound Taper Balloon Shape

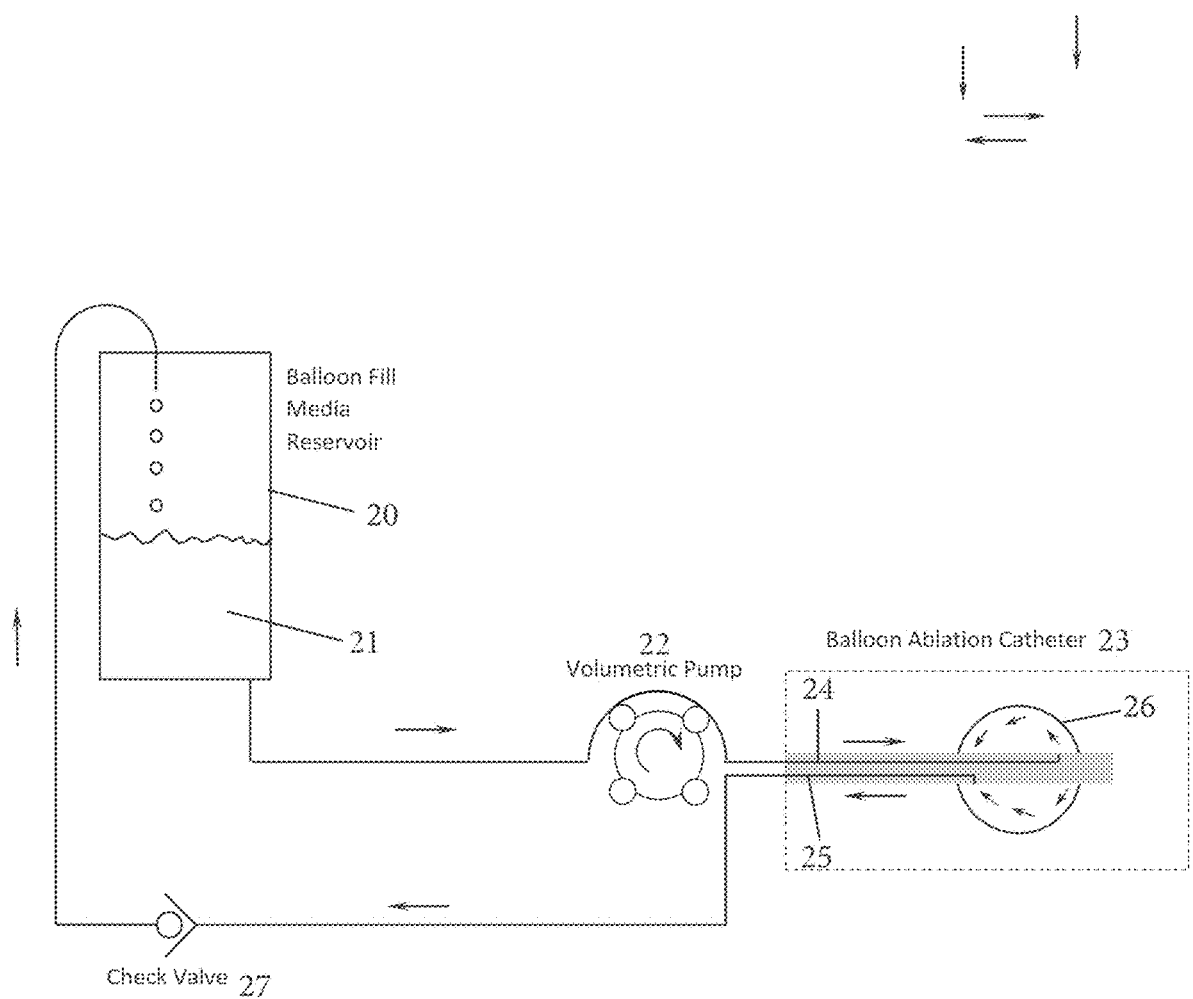
Figure 4. Fluid Management – (Prior Art)

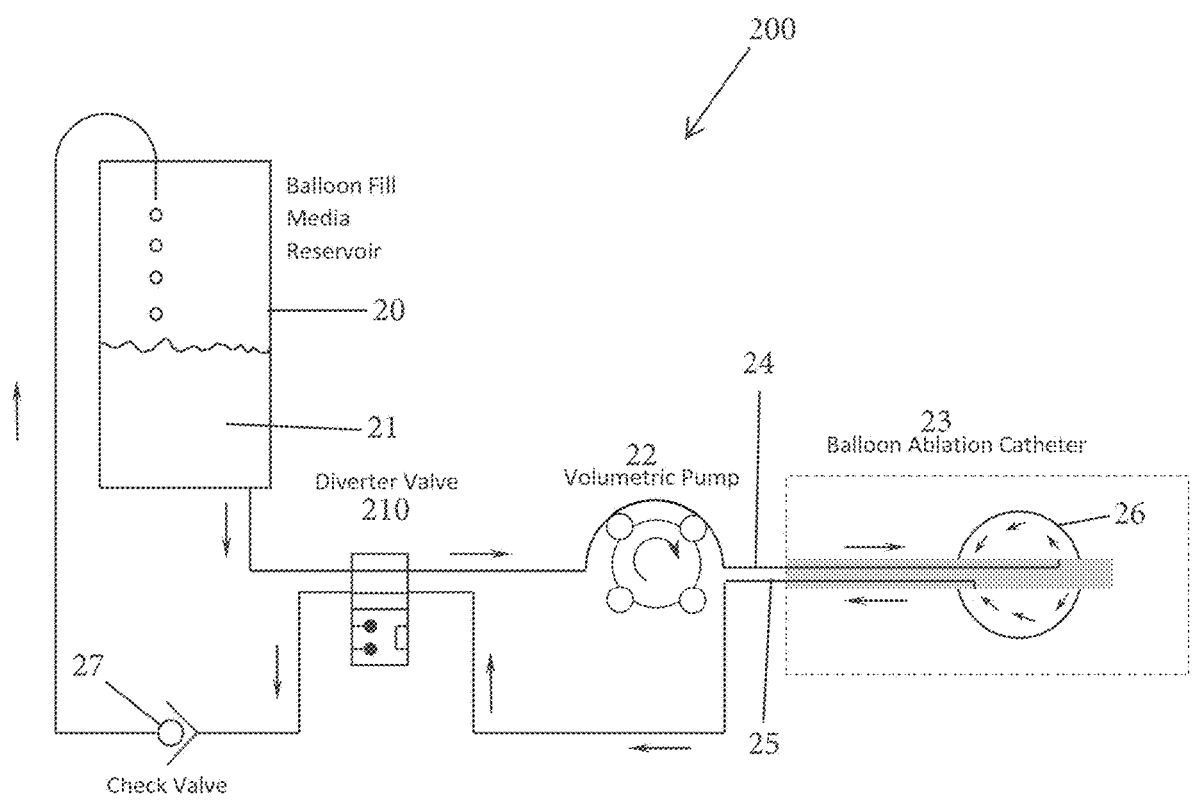
Figure 5. Trapped Volume System in Inflate/Deflate/Purge Mode

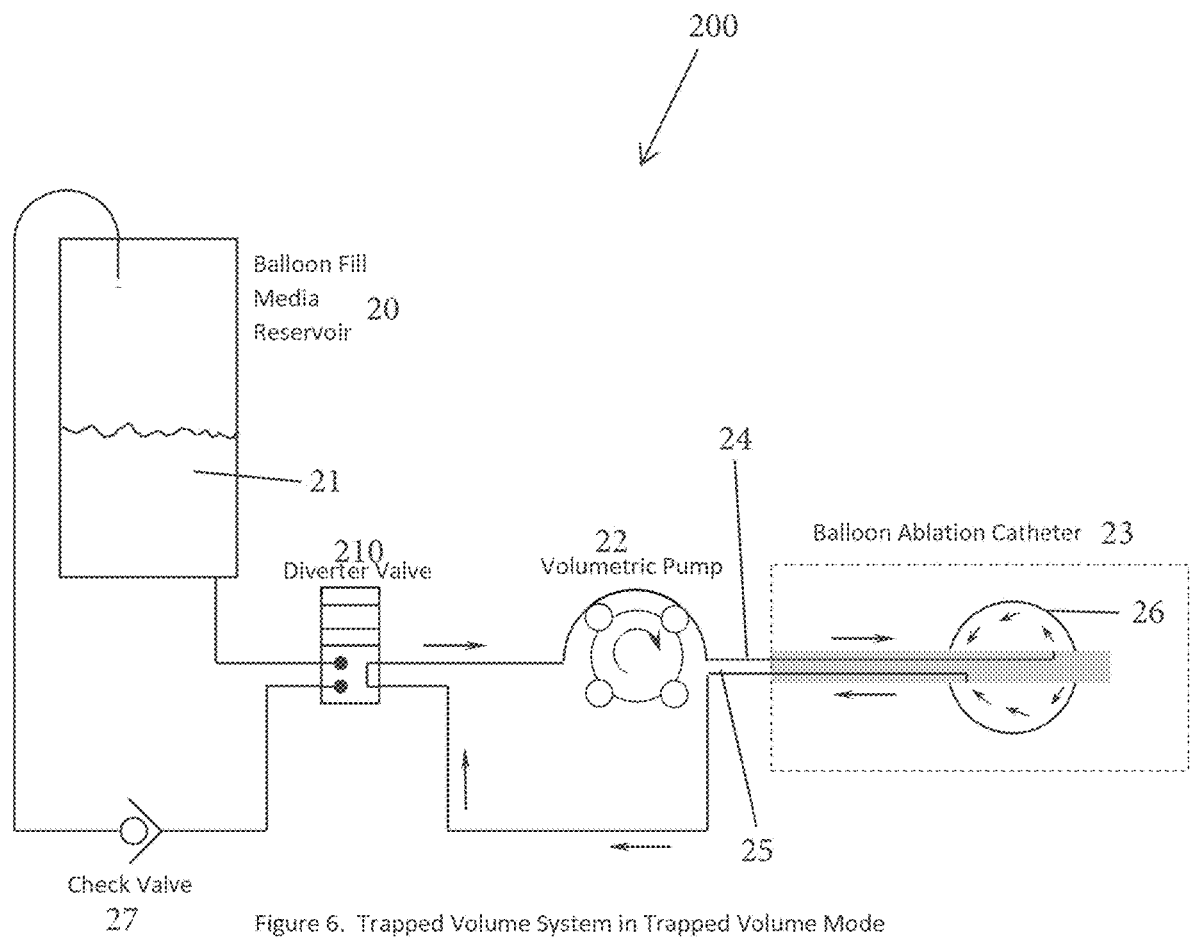
Figure 6. Trapped Volume System in Trapped Volume Mode

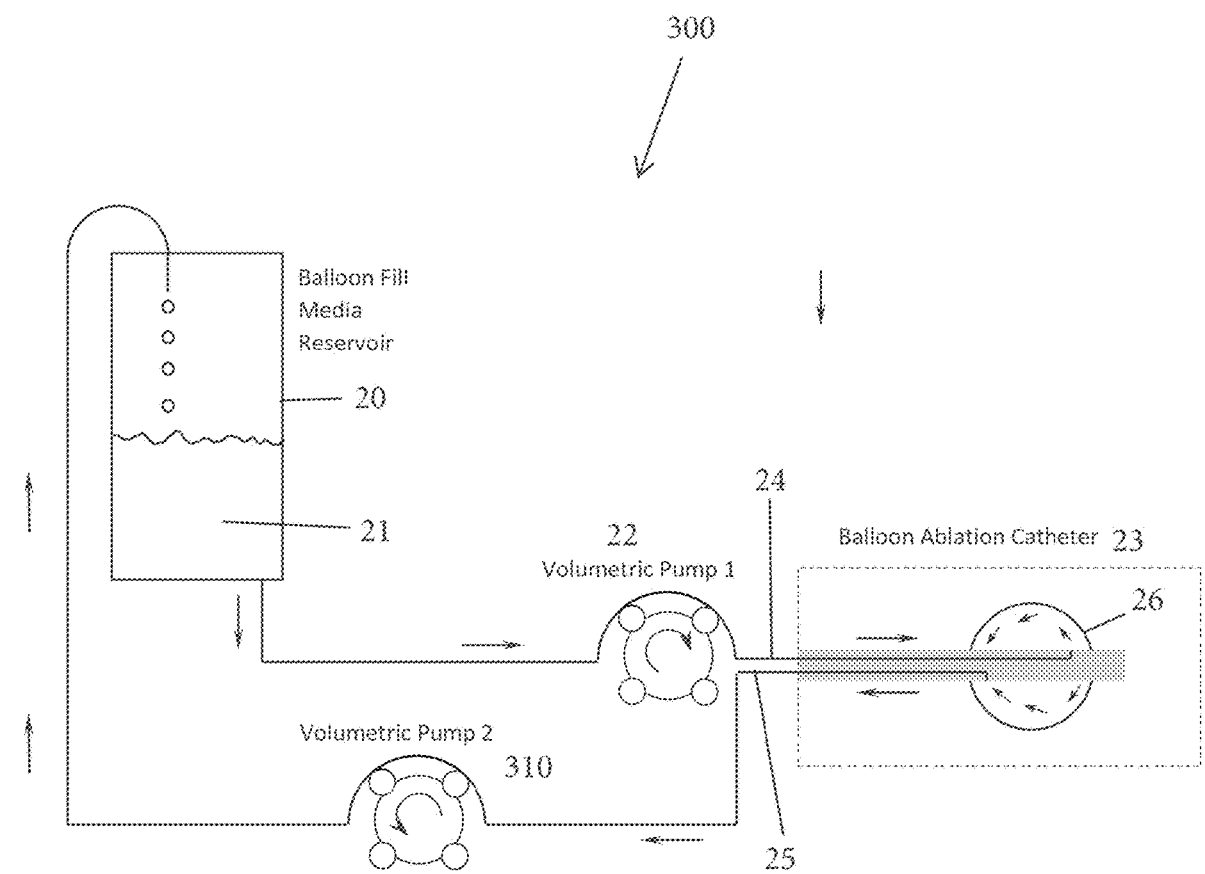
Figure 7. Two Pump Trapped Volume System

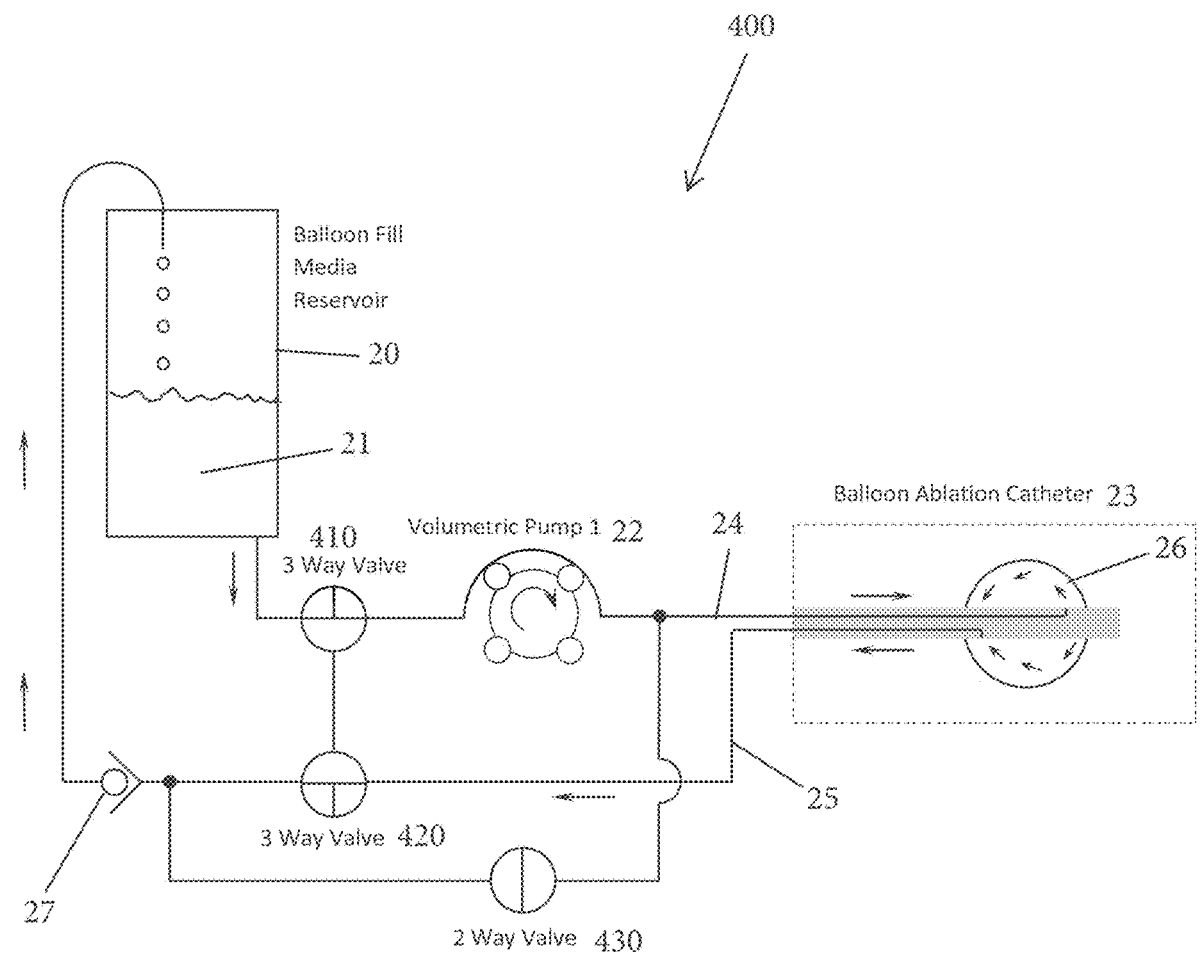
Figure 8. Multi Valve System in Inflate/Deflate/Purge Mode

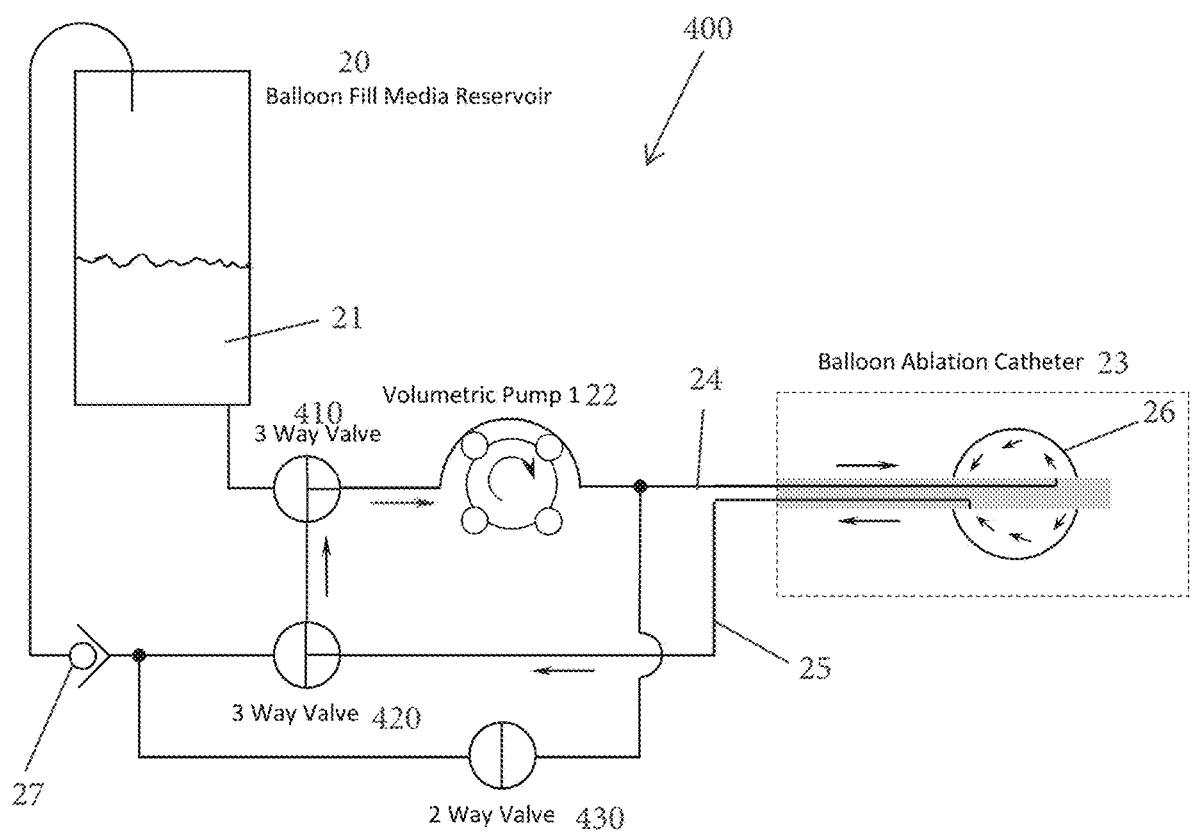
Figure 9. Multi Valve System in Trapped Volume Mode

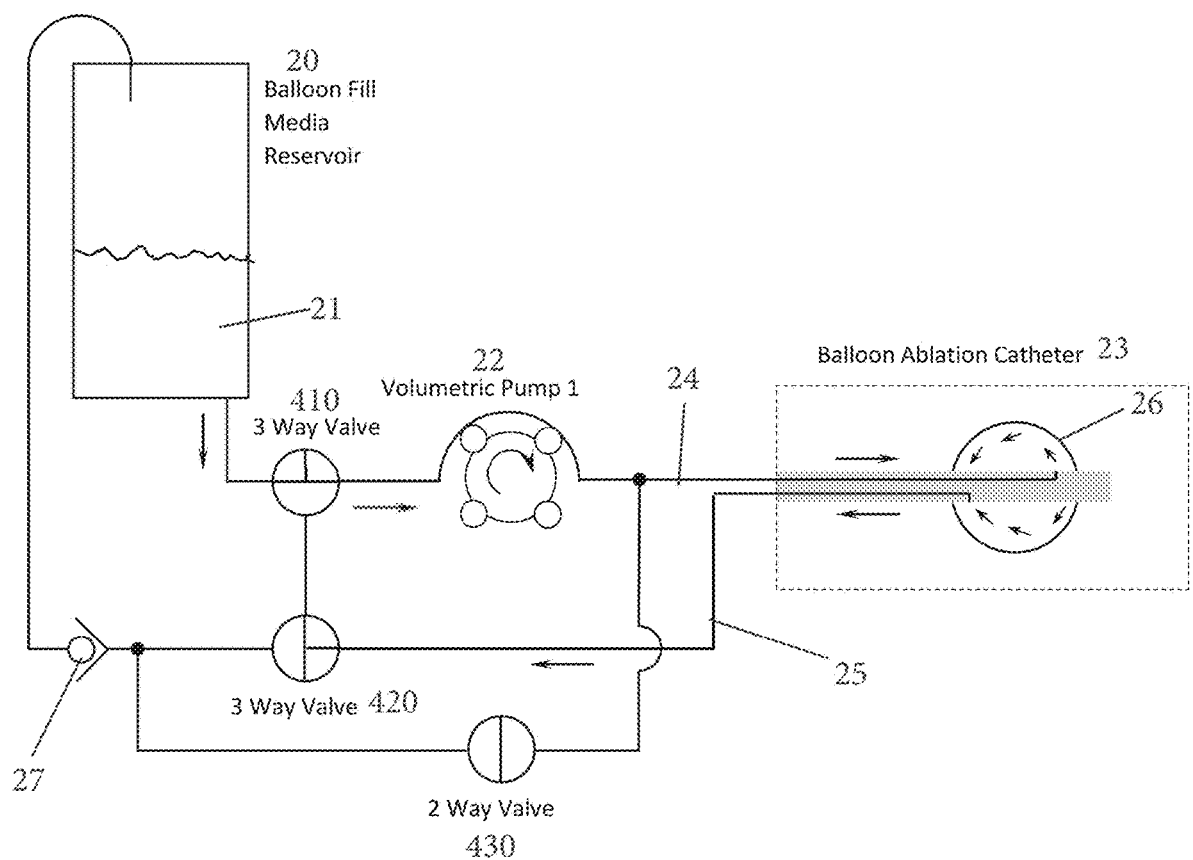
Figure 10. Multi Valve System in Increase Balloon Size Mode

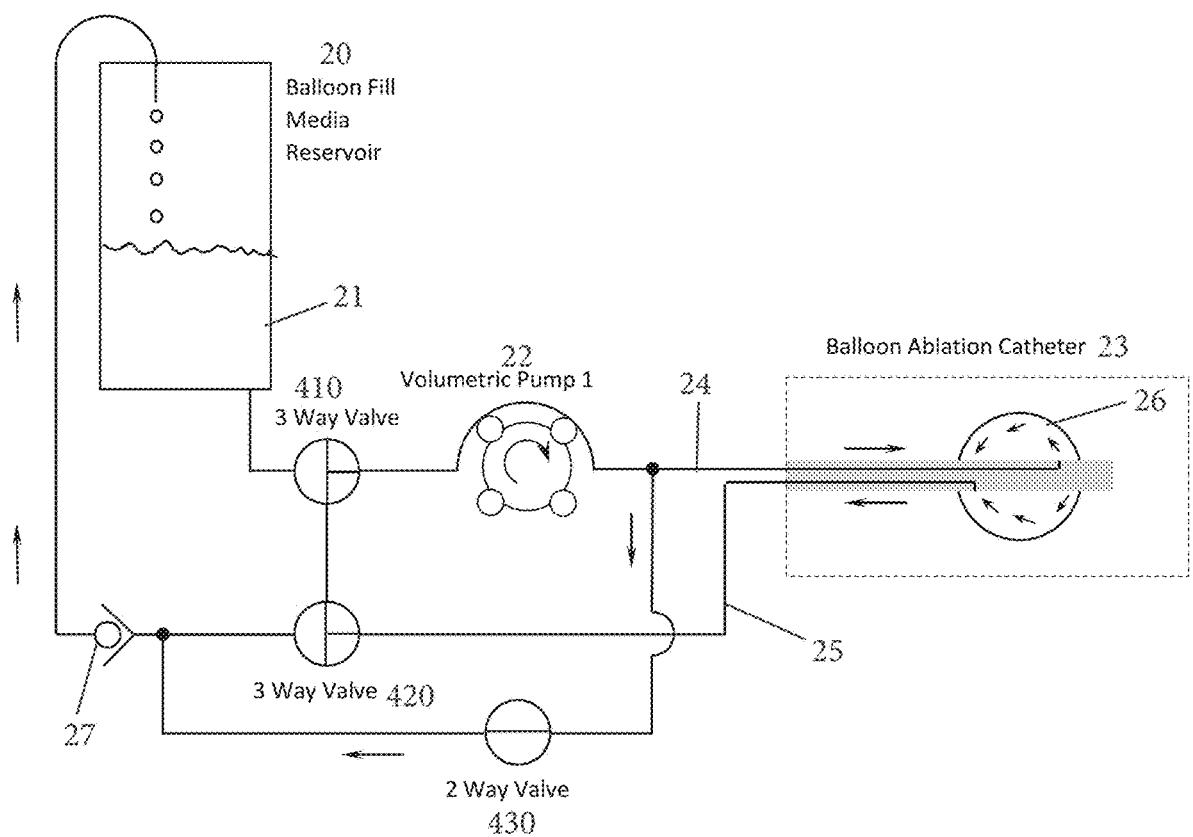
Figure 11. Multi Valve System in Decrease Balloon Size Mode

BALLOON CATHETER AND FLUID MANAGEMENT SYSTEM THEREOF

CROSS-REFERENCE TO RELATED APPLICATION

The present invention is a divisional of U.S. patent application Ser. No. 15/863,264, filed Jan. 5, 2018, now U.S. Pat. No. 11,207,505, which claims priority to U.S. patent application Ser. No. 62/443,270, filed Jan. 6, 2017, all of which are incorporated by reference, as if expressly set forth in their respective entireties herein."

BACKGROUND

This invention relates to balloon catheters and specifically to balloon catheters used to treat atrial fibrillation by creating regions of electrically non-conducting tissue in the region of the left atrium where generally the pulmonary veins join the left atrium. Prior art describes balloon catheters which can ablate tissue in the regions of the pulmonary veins and specifically balloon catheters which ablate tissue using laser energy of 980 nm or similar and also employ a endoscopes positioned inside the balloons of such catheters to view how the balloons contact the atrial tissue. Such endoscopic visualization allows for aiming of the laser energy into tissue contacting the balloon as opposed aiming the laser into areas of the balloon not in contact with atrial tissue since such latter energy delivery would be ineffective at creating lesions which block electrical conduction of the atrial tissue.

SUMMARY

The overall aims of the invention are to provide a balloon catheter system that allows for a much greater area of contact between the balloon and the atrial tissue than is achievable by prior art. Greater area of tissue contact is highly desirable since it allows for more flexibility in choosing locations to deliver laser energy. Such flexibility is desirable to avoid areas adjacent to structures which might be damaged by energy delivery such as the esophagus or the phrenic nerve. A greater area of contact also means that less time must be spent manipulating the balloon in order to achieve a balloon position where contact is adequate to allow for the delivery of the desired pattern of lesions in the region of the pulmonary vein ostium. The invention achieves the aim of increasing balloon to tissue contact area by the following means:
a) Providing a balloon with more compliant material properties.
b) Providing a system that allows the balloon to be inflated such that the pressure in the balloon is substantially lower than prior art allows.
c) Providing a balloon shape that achieves a more stable balloon position when the balloon is placed at the ostium of a pulmonary vein.
d) Providing a balloon shape that more readily conforms to the geometry of the pulmonary vein ostium.

How these means increase tissue contact with the balloon and how these means are implemented in actual practice are described in more detail below.

BRIEF DESCRIPTION OF THE DRAWING FIGURES

FIG. 1 is a schematic showing an exemplary compliant balloon in contact with a pulmonary vein ostium with balloon forces being shown;

FIG. 2 is a side view of a conventional balloon shape;

FIG. 3 is a side view of a compound taper balloon shape;

FIG. 4 is a schematic of a conventional balloon catheter device with a fluid management system;

FIG. 5 is a schematic of a balloon catheter device with a fluid management system according to a first exemplary embodiment;

FIG. 6 is a schematic of the balloon catheter device with fluid management system of FIG. 5 shown in a trapped volume mode;

FIG. 7 is a schematic of a balloon catheter device with a fluid management system according to a second exemplary embodiment;

FIG. 8 is a schematic of a balloon catheter device with a fluid management system according to a third exemplary embodiment;

FIG. 9 is a schematic of the balloon catheter device with fluid management system of FIG. 8 shown in a trapped volume mode;

FIG. 10 is a schematic of the balloon catheter device with fluid management system of FIG. 9 shown in a balloon inflation mode;

FIG. 11 is a schematic of the balloon catheter device with fluid management system of FIG. 9 shown in a balloon deflation mode.

DETAILED DESCRIPTION OF CERTAIN EMBODIMENT

Physics of Balloon Contact with Tissue

Figure 12:
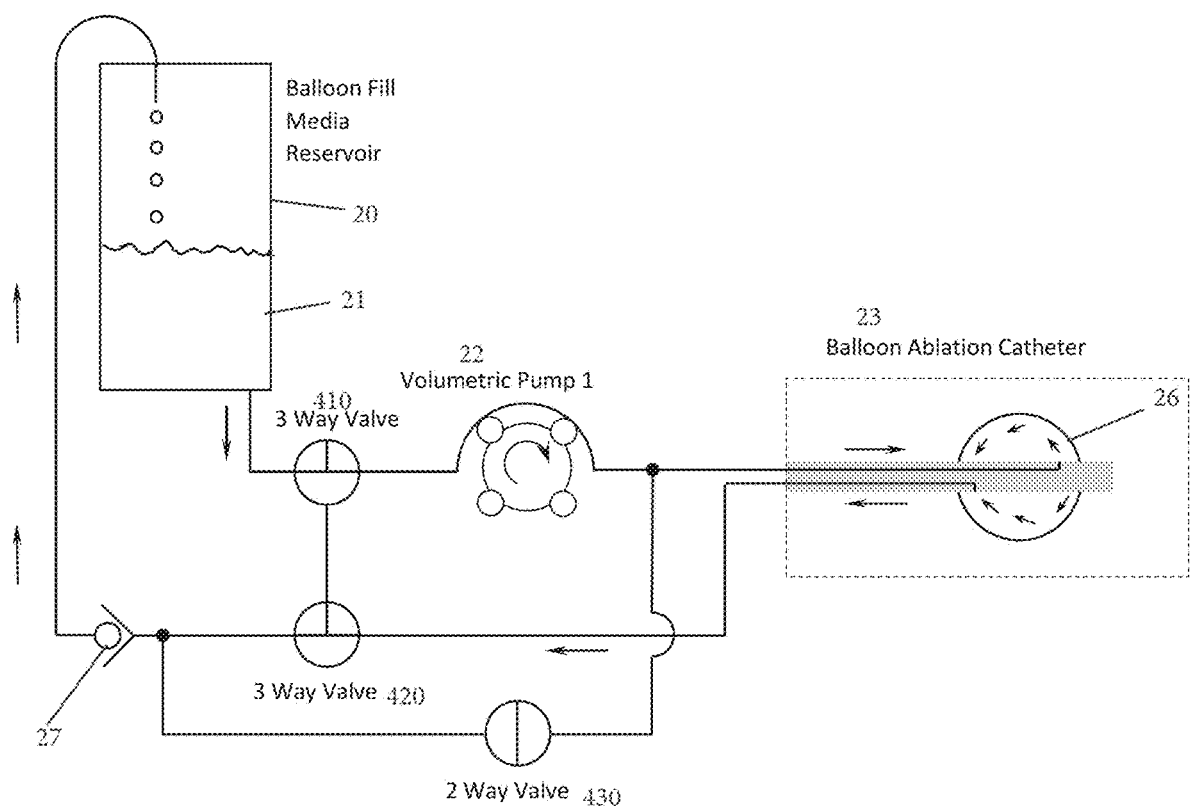
FIG. 12 is a schematic of the balloon catheter device with fluid management system of FIG. 9 shown in a backup mode.

FIG. 1 shows a compliant balloon 100 in contact with a pulmonary vein ostium. Axial force F is applied by the physician manipulating a catheter 10 in order to urge the balloon 100 at the distal end of the catheter toward the pulmonary vein ostium. The balloon 100 makes contact with the atria and pulmonary vein tissue and a contact area of magnitude A is created. Where the balloon 100 contacts tissue there is a contact pressure $P_C$. If the balloon membrane is thin and flexible the balloon material itself imparts negligible mechanical forces on the tissue. Consequently, the contact pressure $P_C$ is essentially equal to the pressure used to inflate the balloon $P_B$. In equilibrium, the axial force F is equal to the projection of the contact area A in the z direction times the balloon pressure $P_B$. For a generally conical tapered balloon shape as shown with a cone half-angle of $\Theta$, the area of contact is given by the equation:

$$A = F/P_B \sin \Theta \qquad \text{Equation 1}$$

From the above equation is can be seen that operating a low balloon pressure is desirable to increase the contact area of the balloon with the tissue. There are practical limits to how much force F can be applied to the catheter shaft. That force must not exceed a force that would damage atrial tissue. There are also practical limits to the taper angle of the balloon $\Theta$. Balloons must interface with pulmonary veins of varying sizes so it is desired that the balloons have small diameter distal ends to be able to enter the smaller veins but the balloon must also have large maximum diameter in order to prevent the balloons form entering too deeply into large veins. If too small a value of theta is selected then the difference between the disal end of the balloon and the maximum diameter will be too small to allow the balloon to interface properly with a greatest range of vein sizes.

Details of the Invention Related to the Balloon

Prior art balloons have been made of elastomeric materials such as Urethane with a durometer of 90 shore A. In use these balloons are inflated to pressures of 2 to 5 PSI. The range of pressure is used in order to adjust the maximum diameter of the balloon in order to create balloon sizes compatible with an even greater range pulmonary vein sizes than is provided for by the tapered shape of the balloon. In use prior art balloons are inflated over the range of pressure stated in order to achieve maximum diameters ranging from 25 mm to 35 mm. The balloons of the current invention employ Urethane, Silicone Rubber or Polyisoprene materials in durometers ranging from 80 Shore A to 50 Shore A. In use, these balloons 100 will be inflated to pressures of 0.2 PSI to 1 PSI. These much lower pressures enable greater contact area to be achieved as described above. The lower material durometers enable the balloons to be inflated to the same range of diameters of 25 mm to 35 mm while still maintaining the lower balloon pressure of 0.2 PSI to 1 PSI desired to achieve greater tissue contact with the balloon. FIG. 2 shows one prior art balloon shape. A balloon of this shape implemented in the materials described above will achieve the aims of the present invention. In addition, it has been found that a shape as shown in FIG. 3 exhibiting a compound taper achieves even greater contact with a typical pulmonary vein ostium. Prior art balloons have tapers which range from 25 degrees to 40 degrees. The compound taper of the present invention has a distal taper $\Theta_1$ of 15 degrees to 25 degrees and a proximal taper $\Theta_2$ of 30 degrees to 55 degrees. It is desirable that the proximal and distal taper regions blend together gradually with a smooth and fair shape as shown.

Details of the Invention Related to the Fluid Management System

The balloons 100 of the balloon catheters 10 described here are inflated with a transparent incompressible fluid. Deuterium Oxide is the fluid of choice since it is very transparent to 980 nm laser energy generally employed. However water, saline and even compressible fluids could be employed instead. The inflation media serves to inflate the balloon and is also continuously circulated through the balloon and catheter in order prevent the balloon and other catheter components from becoming too hot during energy delivery.

FIG. 4 shows an exemplary prior art fluid management system used when the desired balloon inflation pressures range from 2 to 5 PSI. In this system, a reservoir 20 contains a volume of inflation media 21. A volumetric pump 22, such as a peristaltic pump, is used to circulate the inflation media 21 through a balloon catheter 23. Inflation media 21 is fed to the pump 22 from the bottom of the reservoir 20. After passing through the pump 22, the inflation media 21 passes through a length of tubing and enters a supply lumen 24 of the multi-lumen balloon catheter 10. The supply lumen 24 terminates at an opening inside a balloon 26 allowing inflation media 21 to enter the balloon 26. Inflation media 21 fills the balloon 26, circulates through the balloon 26 and exits the balloon 26 through a second lumen 25 in the multi lumen balloon catheter 10. From here fluid returns to the reservoir 20 via a second tube.

In this system, the balloon pressure is regulated by changing the speed of the volumetric pump 22. For a given pump speed pressure, the balloon 26 will increase until equilibrium is reached where the pressure in the balloon 26 is sufficient to create a return flow rate back to the reservoir 20 through the second (return) lumen 25 in the multi-lumen catheter and the tubing back to the reservoir 20 that matches the flow rate of the volumetric pump 22. In general, the flow rates and lumen sizes are such that laminar flow exists in the flow passages when Deuterium Oxide or water is used as the inflation media 21. The laminar flow regime creates a condition where the balloon pressure is directly proportional to the flow rate from the volumetric pump 22.

To deflate the balloon 26, the volumetric pump 22 is run in reverse. A check valve 27 is provided to prevent air from entering the balloon 26 during balloon deflation. It should also be noted that separate pathways are used to withdraw inflation media 21 from the reservoir 20 and to return it to the reservoir 20. In this way any air in the balloon 26 or fluid pathways is expelled from the system during the initial phase when inflation media 21 is introduced into a new dry catheter 10. Any air in the catheter fluid passages returns to the reservoir 20 along with the inflation media 21 and is dissipated as is exits the return tube shown in the figure returning drops of inflation media 21 to the reservoir 20.

The prior art fluid management system is not suitable for use in the present invention where the desired balloon inflation pressures are only 0.2 PSI to 1 PSI. To achieve these low pressures with the prior art system the flow rate must be reduced to a low flow rate that is no longer adequate to cool the balloon and catheter components sufficiently. Additionally, since balloon pressure and axial force on the balloon catheter are related as shown in FIG. 1 and equation 1, balloon pressure may be transiently increased by transiently increasing axial force as unavoidably occurs during a procedure. The source of such transient increases are numerous and include patient breathing, Physician adjustments to the force on the catheter and physician fatigue. This transient increase causes the inflation media outflow to increase and allows the balloon to deflate slightly. For balloon pressures of 2 PSI to 5 PSI these transient changes in balloon pressure and balloon inflation are not significant nor noticeable but, at significantly lower pressures of 0.2 PSI to 1 PSI the effects are large enough that the balloon may deflate enough for wrinkles to appear in the balloon and for the balloon position at the pulmonary vein ostium to change. Both these conditions are undesirable. The present invention addresses these problems as described below.

FIG. 5 shows a fluid management system 200 according to at least one implementation of the present invention that avoids the problems detailed above. The system 200 includes a number of components that are illustrated in FIG. 4 and therefore, like elements are numbered alike.

In this system 200, a diverter valve 210 is added to the prior art system of FIG. 4. The diverter valve 210 is a two-position valve. When in the position shown in FIG. 5, the diverter valve 210 allows the system 200 to function identically to the prior art system of FIG. 4. The balloon 26 may inflated to a given pressure by adjusting the volumetric pump speed 22. Deflation is achieved by reversing the pump 22 and air elimination occurs in a manner identically to the prior art system. Once the balloon 26 is inflated to the desired pressure as determined by observing the endoscopic image or by observing the change in the level of inflation media in the reservoir (or by other means such as observing a fluoroscopic or echocardiographic image of the balloon residing the patient), the diverter valve 210 is repositioned to the position shown in FIG. 6.

In this configuration of FIG. 6, the inflation media 21 filling the catheter 23 and balloon 26 is recirculated through the catheter 10 in a closed loop fashion. In this mode, a specific volume of inflation media 21 is "trapped" in the balloon catheter 23 and associated tubing. Hence, the volume of inflation media 21 filling the balloon 26 will not change if the pump speed is changed or if the axial force on the catheter 23 is transiently altered. While in this mode, the pump speed may be increased to that necessary to achieve a desired level of cooling and this will have no effect on the balloon pressure or size. In actual operation with the system 200 running as shown in FIG. 4 (Inflate/Deflate/Purge Mode), balloon inflation pressure of 0.2 PSI to 1 PSI will be achieved with pump flow rates of 2 ml/minute to 10 ml/minute. The minimum flow rate necessary to achieve the required level of cooling is 10 ml/minute. To achieve this level of flow during laser energy delivery, first the balloon 26 is inflated to the desired pressure or volume, trapped volume mode is then entered and then the pump speed is increased to at least 10 ml/minute.

It is worth noting that when the system 200 is in trapped volume mode, the volumetric pump 22 may create less than atmospheric pressure at the pump intake (this is the left side of the pump as it is shown in FIGS. 5 and 6.) Generally, the faster the volumetric pump 22 runs, the lower the pressure at the intake side of the pump. The pump speed must not be increased beyond that speed which will create an intake pressure lower than the vapor pressure of the inflation media or create a pressure so low that that pressure will cause gas dissolved in the inflation media to come out of solution and form gas bubbles. Limiting the pump intake pressure to no lower than 5 PSI below atmospheric pressure will prevent dissolved gas outgassing or inflation media vaporization. Pump speeds of 50 ml/minute or less will achieve the desired limit on intake vacuum. This flow rate is more than adequate to provide adequate cooling for the catheter.

FIG. 7 shows an additional method of balloon inflation media management system 300. Here the diverter valve 210 has been replaced by a second volumetric pump 310. In this system 300, all the necessary functions of the inflation media management system 300 are accomplished by control of the speed and direction of the first and second volumetric pumps 22, 310. To initially inflate the balloon 26, the first pump 22 runs in the direction shown in FIG. 7. To purge air form the system 300, both the first pump 22 and the second pump 310 run at the same speed after the balloon 23 has been initially inflated. To increase the balloon size, the first pump 22 is run faster than the second pump 310 for a brief interval. To decrease the balloon size, the second pump 310 is run faster than the first pump 22 for a brief interval. Once any desired balloon size is achieved, the first and second pumps 22, 310 can be run at the same speed to maintain the balloon size at any desired flow rate. This mode is identical to the "trapped volume mode" described above for the system in FIGS. 5 and 6. To rapidly deflate the balloon 26, the first and second pumps 22, 310 are run in the reverse direction from that shown in FIG. 7. Ideally, the two pumps 22, 310 are connected to a control system so that the coordinated actions of the two pumps 22, 310 are achieved by touching control buttons that create the necessary pump actions for balloon inflation, purging, size increase, size decrease, cooling during ablation at constant balloon size and deflation.

FIG. 8 shows another system 400 with similar operation to the system shown in FIGS. 5 and 6 and therefore like numbers are used for like elements. For the system 400 in FIG. 8, the diverter valve has been replaced by two three-way valves, namely a first three-way valve 410 and a second three-way valve 420. Such valves have connections for three different flow passages and, depending on the position of the valve 410, 420, allow any two passages to be interconnected with the third passage being dead-ended. In addition, a third two-way valve 430 (or open-closed valve) has been added whose function is described below.

FIG. 8 shows the system 400 with the valves 410, 420, 430 positioned so the system 400 is in the Inflate/Deflate/Purge Mode. The system as shown will operate identically to the system shown in FIG. 4. The degree of balloon inflation is determined by the pump speed. Running the pump in reverse will deflate the balloon 26. With the pump running in the forward direction, air is easily purged from the system. Changing the positions of the three-way valves 410, 420 to that shown in FIG. 9 switches the system 400 to trapped volume mode with identical operation to the system 400 shown in FIG. 6. Here the balloon inflation state is independent of pump speed and transient changes to the axial force on the catheter 23 will not alter the inflation state of the balloon 26. Further changing the position of the uppermost three-way valve 410 to that shown in FIG. 10 allows the balloon size to be increased. Once the desired increased size is achieved the uppermost three-way valve 410 is positioned back to the position shown in FIG. 9. Finally, if the two-way valve 430 is opened as shown in FIG. 11, the balloon size will decrease. FIG. 12 shows a backup mode in which fluid flows to the catheter 23 and is retuned back to the reservoir 20. The two-way valve 430 is closed, while the three-way valve 410 is open and the three-way valve 420 is also open.

Other valve and pump schemes are possible to achieve the functions described above. For example, the valving functions can easily be achieved by using readily available solenoid operated pinch valve actuators which serve to punch closed standard PVC medical tubing.

With all the described inflation media management systems, the valves and pumps are ideally connected to an automatic control system that allows the desired operations (Purge, Inflate, Increase Balloon Size, Decrease Balloon Size, Deflate and Trapped Volume Mode) to be easily achieved with the press or touch of a button. Ideally such a control system can be fitted with a sterile transparent drape so the fluid control operations can be performed by an operator who scrubbed in and operating the catheter at the same time. However, the systems described are perfectly useful with the valves and pumps being operated individually and manually.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A balloon catheter system comprising:
a balloon catheter including a catheter body and an inflatable balloon coupled to one end thereof; and
a fluid management system for controllably inflating and deflating the balloon, the fluid management system including a reservoir for storing balloon fill media, a first conduit connected between the reservoir and the balloon for delivering the balloon fill media, a second conduit connected between the balloon and the reservoir for returning the balloon fill media from the balloon to the reservoir, a first pump disposed along the first conduit and configured to circulate the balloon fill media along a circuit defined by the first and second conduits, the fluid management system further including a diverter valve that is disposed along the first and second conduits, with the first pump being disposed along the first conduit between the diverter valve and the balloon, the diverter valve being configured for placement in a first position and a second position, wherein in the first position, the balloon fill media freely flows through the first conduit from the reservoir to the balloon and freely flows through the second conduit from the balloon back to the reservoir, and wherein in the second position, the balloon fill media is recirculated through the balloon catheter in a closed loop manner and is prevented from flowing back to the reservoir from the balloon.

2. The balloon catheter system of claim 1, wherein a pump speed of the first pump is adjusted to control a level of cooling of the balloon fill media.

3. The balloon catheter system of claim 1, wherein the first pump comprises a peristaltic pump.

4. The balloon catheter system of claim 1, further including a check valve disposed along the second conduit between the diverter valve and the reservoir.

5. A balloon catheter system comprising:
a balloon catheter including a catheter body and an inflatable balloon coupled to one end thereof, wherein the balloon is formed of a material selected from the group consisting of urethane, silicone rubber and polyisoprene and has a durometer between 80 Shore A and 50 Shore A, wherein the balloon has a distal taper of 15 degrees to 25 degrees and a proximal taper of 30 degrees to 55 degrees; and
a fluid management system for controllably inflating and deflating the balloon, the fluid management system including a reservoir for storing balloon fill media, a first conduit connected between the reservoir and the balloon for delivering the balloon fill media, a second conduit connected between the balloon and the reservoir for returning the balloon fill media from the balloon to the reservoir, and a pump disposed along the first conduit and configured to circulate the balloon fill media along a circuit defined by the first and second conduits;
wherein the fluid management system includes a selectable valve that permits the balloon to be inflated by delivering the balloon fill media to the balloon; to be deflated by removing the balloon fill media from the balloon and permits the balloon fill media to be circulated in a closed loop which is not in fluid communication with the reservoir.

6. The balloon catheter system of claim 5, wherein the pump has a pump flow rate of 2 ml/minute to 10 ml/minute.

7. The balloon catheter system of claim 5, wherein the fluid management system further includes a diverter valve that is disposed along the first and second conduits, with the first pump being disposed along the first conduit between the diverter valve and the balloon, the diverter valve being configured for placement in a first position and a second position, wherein in the first position, the balloon fill media freely flows through the first conduit from the reservoir to the balloon and freely flows through the second conduit from the balloon back to the reservoir, and wherein in the second position, the balloon fill media is recirculated through the balloon catheter in a closed loop manner and is prevented from flowing back to the reservoir from the balloon.

8. The balloon catheter system of claim 5, wherein in the closed loop, the first and second conduits are fluidly connected with a third conduit.

* * * * *